(12) United States Patent
Komatsubara

(10) Patent No.: US 9,216,119 B2
(45) Date of Patent: Dec. 22, 2015

(54) ABSORBENT ARTICLE FOR PET ANIMALS AND PACKAGE THEREOF

(71) Applicant: UNICHARM CORPORATION, Shikokuchuo-shi, Ehime (JP)

(72) Inventor: Daisuke Komatsubara, Kanoji (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 14/385,581

(22) PCT Filed: Jun. 16, 2014

(86) PCT No.: PCT/JP2014/065949
§ 371 (c)(1),
(2) Date: Sep. 16, 2014

(87) PCT Pub. No.: WO2015/001946
PCT Pub. Date: Jan. 8, 2015

(65) Prior Publication Data
US 2015/0045762 A1   Feb. 12, 2015

(30) Foreign Application Priority Data
Jun. 6, 2014   (JP) ................. 2014-118170

(51) Int. Cl.
| | | |
|---|---|---|
| *A61F 13/15* | (2006.01) | |
| *A61F 13/58* | (2006.01) | |
| *A01K 23/00* | (2006.01) | |
| *A61F 13/49* | (2006.01) | |
| *A61F 13/551* | (2006.01) | |
| *A61F 13/56* | (2006.01) | |

(52) U.S. Cl.
CPC ................. *A61F 13/58* (2013.01); *A01K 23/00* (2013.01); *A61F 13/49001* (2013.01); *A61F 13/55115* (2013.01); *A61F 13/5622* (2013.01); *A61F 2013/15186* (2013.01); *A61F 2013/5666* (2013.01); *A61F 2013/583* (2013.01)

(58) Field of Classification Search
CPC ................. A01K 23/00; A61F 13/5622; A61F 2013/15186
USPC ........................................ 604/385.01, 385.09
See application file for complete search history.

(56) References Cited

FOREIGN PATENT DOCUMENTS

| EP | 2721924 | * | 4/2014 | ............ A01K 23/00 |
|---|---|---|---|---|
| JP | 2007-020533 | A | 2/2007 | |
| JP | 2009-254278 | A | 11/2009 | |
| JP | 2013-000035 | A | 1/2013 | |

OTHER PUBLICATIONS

International Search Report mailed Jul. 22, 2014 in International Application No. PCT/JP2014/065949 filed Jun. 16, 2014.
Notification of Reason for Refusal mailed Jul. 15, 2014 in corresponding Japanese Application No. 2014-118170.

* cited by examiner

*Primary Examiner* — Jacqueline Stephens
(74) *Attorney, Agent, or Firm* — Hauptman Ham, LLP

(57) ABSTRACT

An absorbent article and a package thereof are provided for a pet animal without a possibility that a fastener might be exposed on the outer side of the article. The absorbent article includes an absorbent panel and a fastener for fastening the absorbent panel. The absorbent panel has an absorbent region in which an absorbent body is disposed, a first non-absorbent region extending from the absorbent region to a first end edge and a second non-absorbent region extending from the absorbent region to a second end edge. The fastener is allocated on an exterior surface in the first non-absorbent region and releasably grabbed by the exterior surface of the absorbent panel except the first non-absorbent region to maintain such folded state when the absorbent panel is folded until the interior surface of the first non-absorbent region faces the interior surface of the second non-absorbent region.

7 Claims, 12 Drawing Sheets

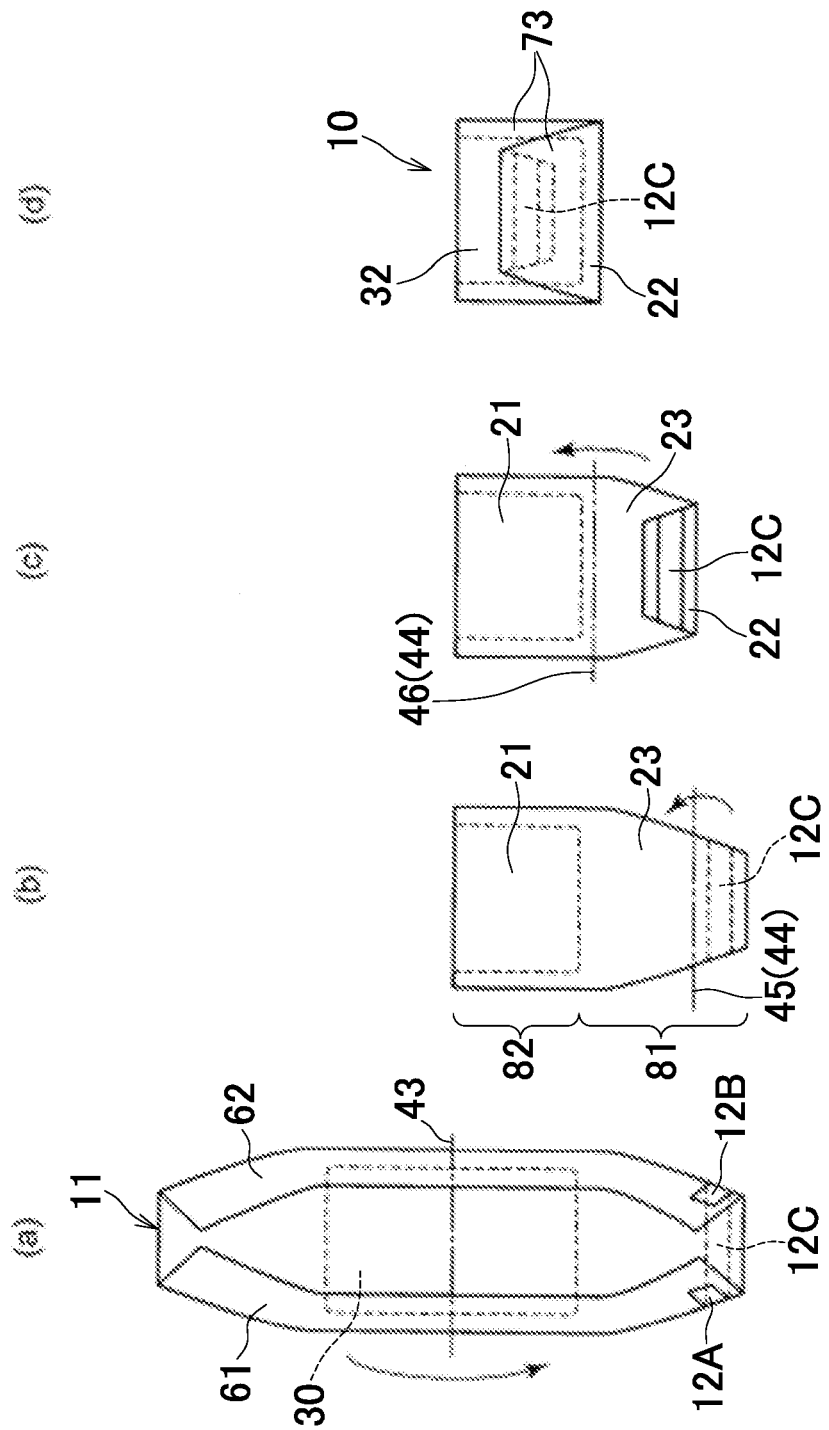

ABSORBENT ARTICLE FOR PET ANIMALS AND PACKAGE THEREOF

RELATED APPLICATIONS

The present application is a National Phase of International Application Number PCT/JP2014/065949, filed Jun. 16, 2014, which claims priority to Japanese Application Number 2014-118170, filed Jun. 6, 2014.

TECHNICAL FIELD

The present invention relates to absorbent articles for pet animal and packages thereof.

BACKGROUND

Conventionally, packages are known including a packaging bag and absorbent articles for pet animals, each folded back on itself, contained in the packaging bag. For example, a package of absorbent articles for pet animals disclosed in Patent Literature 1 includes the absorbent articles each having an absorbent panel and fastening means serving to releasably fasten both ends of the absorbent panel to each other when the article is put on a body of pet animal and a packaging bag adapted to contain a plurality of the absorbent articles. The absorbent panel has a topsheet lying on the side of an interior surface, a backsheet lying on the side of an exterior surface and an absorbent body interleaved between the top- and backsheets wherein the backsheet is provided on the side of its exterior surface with a mechanical fastener as a fastening system. A plurality of the absorbent articles, each doubled-up with the backsheet exposed on the outer side, are contained within the bag in a stacked state.

CITATION LIST

Patent Literature

{PTL 1}: JP 2013-000035 A

SUMMARY

Technical Problem

In the absorbent article for pet animal disclosed in Patent Literature 1, the fastener is arranged on the exterior surface of the absorbent panel and consequently there is no anxiety that the fastener of the absorbent article put on the body of pet animal might come in contact with the body of pet animal and create a feeling of discomfort against the body.

However, the fastener is exposed on the outer side of the absorbent article when the absorbent article is doubled up may cause undesirable situations. For example, dust adhering to the exposed fastener may deteriorate the fastening strength of the fastener or each pair of the adjacent doubled-up absorbent articles within the packaging bag may unintentionally stick to each other by the intermediary of the respective fasteners exposed on the outer side and make it difficult to take out the absorbent articles one by one from the packaging bag.

An object of the present invention is to improve the prior art and to provide an absorbent article for pet animal free from the possibility that the fastener might be exposed on the outer side when the article is doubled up and a package thereof

Solution to Problem

According to a first aspect of the present invention, there is provided an absorbent article for pet animal having a longitudinal direction and a transverse direction being orthogonal to each other and an interior surface and an exterior surface opposite to the interior surface, and including an absorbent panel provided with a liquid-permeable topsheet lying on the side of the interior surface and a liquid-impermeable backsheet lying on the side of the exterior surface, and further including a fastening system functioning to releasably fasten predetermined regions of the absorbent panel to each other.

In such absorbent article, the first aspect of the present invention lies in that the absorbent panel has a first end edge and a second end distanced from each other in the longitudinal direction and extending in the transverse direction, a first non-absorbent region extending from the absorbent region to the first end edge and a second non-absorbent region extending from the absorbent region to the second end edge; and the fastening system includes a fastener as an constituent thereof allocated on the exterior surface in the first non-absorbent region and, in a state of the absorbent panel folded at least in a manner that the interior surface of the first non-absorbent region faces the interior surface of the second non-absorbent region, the fastener is releasably caught by the exterior surface of the absorbent panel except the first non-absorbent region to maintain the folded state.

A second aspect of the present invention relates to a package containing a plurality of the absorbent articles for pet animal.

The second aspect of the present invention is characterized in that the absorbent panel is folded along an imaginary first transverse fold line in the absorbent region until the first non-absorbent region and an interior surface of the second non-absorbent region come in contact with each other and, in such folded state, further folded along an imaginary second transverse fold line in a lapped-over portion in which the first non-absorbent region and the second non-absorbent region are lapped over each other; and the absorbent article is maintained in the state folded along the imaginary first and second transverse fold lines by the intermediary of the fastener and the fastener is not caught by the other absorbent articles within the package.

Advantageous Effects of Invention

According to one or more embodiments of the absorbent article for pet animal according to the first aspect of the present invention, the fastener is provided on the exterior surface in the first non-absorbent region and, in the folded state of the absorbent panel so that the interior surface of the first non-absorbent region and the interior surface of the second non-absorbent region face each other, releasably caught by the exterior surface of the absorbent panel except the first non-absorbent region and thereby maintains the diaper in folded state. In this way, the fastener is not exposed in the folded state of the diaper.

According to one or more embodiments of the package according to the second aspect of the present invention, the absorbent panel is folded along an imaginary first transverse fold line in the absorbent region until the first non-absorbent region and an interior surface of the second non-absorbent region come in contact with each other and, in such folded state, further folded along an imaginary second transverse fold line in a lapped-over portion in which the first non-absorbent region and the second non-absorbent region are lapped over each other and the absorbent article is maintained in the state folded along the imaginary first and second transverse fold lines by the intermediary of the fastener and the fastener is not caught by the other absorbent articles within the package. In this way, the fastener is not exposed in the folded state of the diaper and, for this reason, it is easy to take out the absorbent articles from the packaging bag one by one.

BRIEF DESCRIPTION OF DRAWINGS

The drawings illustrate specific embodiments of the present invention including optional and preferred embodiments as well as essential features of the invention.

FIG. 13 (a) through FIG. 13 (d): diagram exemplarily illustrating still another method of folding the diaper.

DESCRIPTION OF EMBODIMENTS

Figure 2:
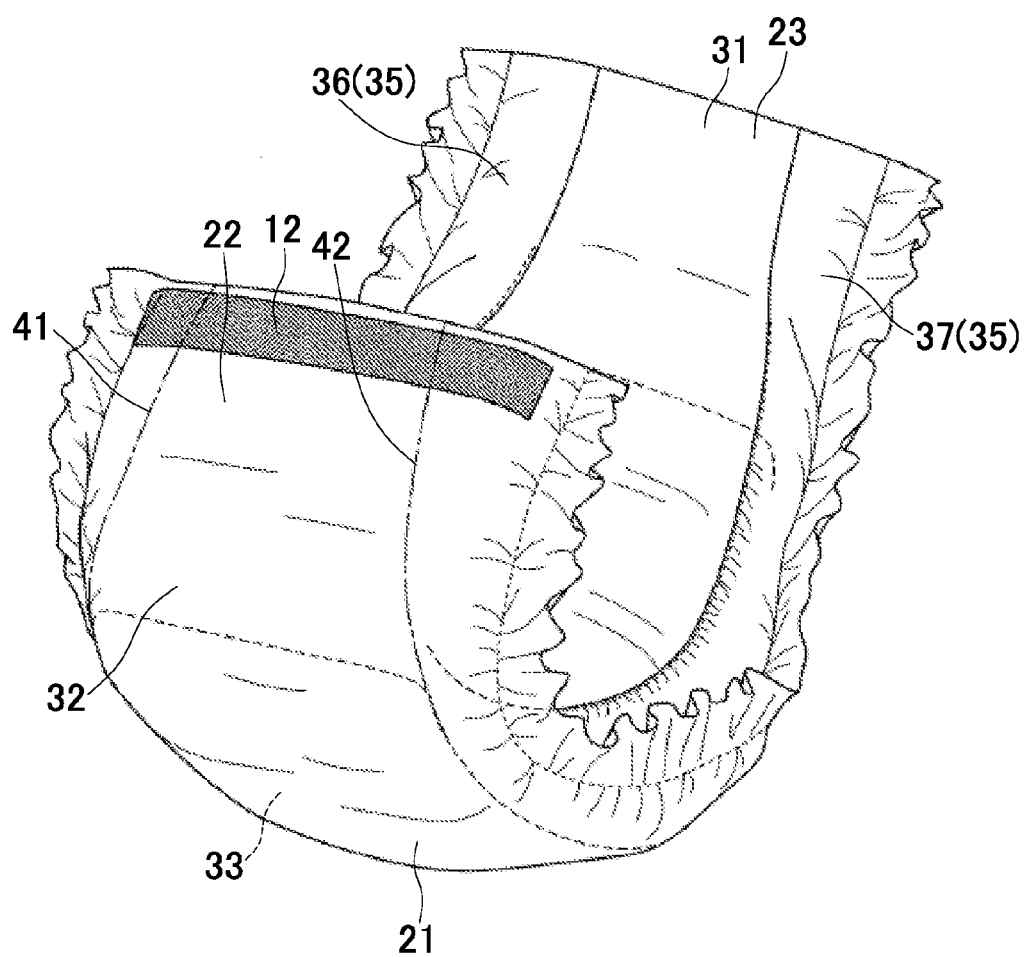
FIG. 2 is a developed perspective view of the diaper.
Figure 3:
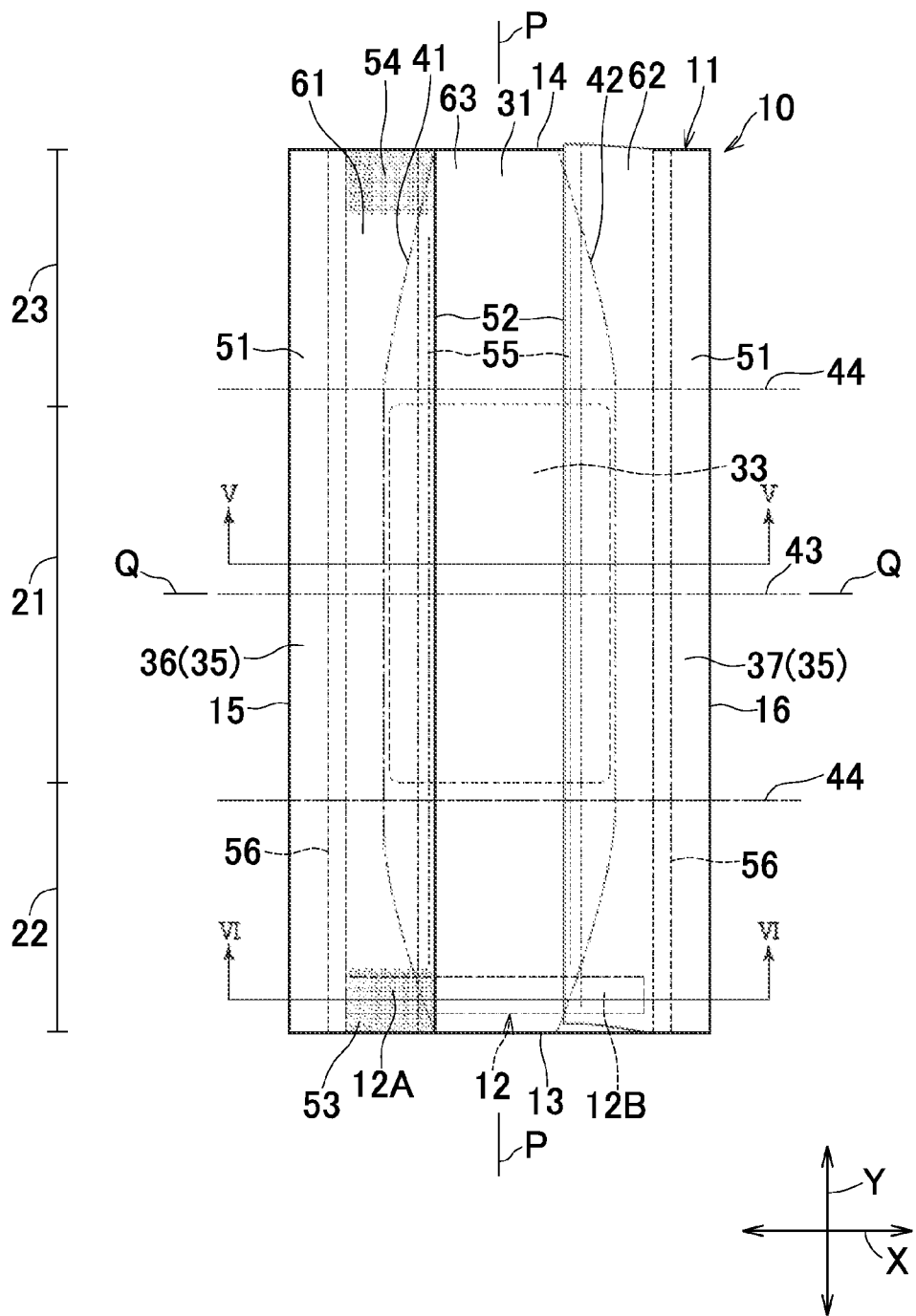
FIG. 3 is a developed perspective view of the diaper as viewed from the side of its interior surface.

The embodiments described relates to an absorbent article for pet animal and a package thereof as illustrated in FIGS. 1 through 13, including both optional and preferred features as well as those features which are essential features of the invention.
In FIGS. 2 and 3, respective elastic elements described later are in a state such that these elastic elements have been stretched until gathers normally developed in respective portions of the article to which the respective elastic elements secured approximately disappear for human faculty of sight.

Referring to FIGS. 1 through 6, a diaper 1 as an example of the absorbent article for pet animal according to the present invention has a longitudinal direction Y and a transverse direction X being orthogonal to each other, a longitudinal axis P bisecting a length dimension in the transverse direction X, a transverse axis Q bisection a length dimension in the longitudinal direction Y, an interior surface facing a body of pet animal, an exterior surface opposite thereto, an imaginary first and second longitudinal fold lines (a pair of longitudinal fold lines) 41, 42 and imaginary first and second transverse fold lines 43, 44. The diaper 10 includes an absorbent panel 11 defining an external form of the diaper 10 and a fastener 12 as a constituent of a fastening system for releasably fastening predetermined regions, preferably, both ends of the absorbent panel 11 to each other.

The absorbent panel 11 includes a liquid-permeable topsheet 31 having a first end edge 13 and a second end edge 14 distanced from each other in the longitudinal direction Y and extending in the transverse direction X, a first side edge 15 and a second side edge 16 distanced from each other in the transverse direction X and extending in the longitudinal direction Y, a liquid-impermeable backsheet 32, an absorbent body 33 lying between the top- and backsheets 31, 32 and a hardly-liquid-permeable or liquid-impermeable leakage-barrier sheet 34 lying between the absorbent body 33 and the backsheet 32. The topsheet 31 is provided on its interior surface side with a pair of containment sheets 35 distanced from each other in the transverse direction X and extending in the longitudinal direction Y. The absorbent panel 11 further includes an absorbent region 21 in which the absorbent body 33 is disposed, a first non-absorbent region 22 extending from the absorbent region 21 to the first end edge 13 and a second non-absorbent region 23 extending from the absorbent region 21 to the second end edge 14 as viewed in the longitudinal direction Y and, in addition, has first and second folded lateral portions (a pair of the folded lateral portions) 61, 62 folded inward along first and second longitudinal fold lines and a central portion 63 defined between the first and second folded lateral portions 61, 62. An imaginary first transverse fold line 43 overlaps the absorbent region 21 and an imaginary second transverse fold line 44 overlaps the first non-absorbent region 22 and/or the second non-absorbent region 23.

The first and second folded lateral portions 61, 62 are distanced from each other in the transverse direction X. The first folded lateral portion 61 lies on the side of the first side edge 15 and the second folded lateral portion 62 lies on the side of the second side edge 16. The first folded lateral portion 61 has a first end portion 61A and a second end portion 61B (opposite ends in the longitudinal direction Y) distanced from each other in the longitudinal direction Y and an intermediate portion 61C extending between the first and second end portions 61A, 61B. The second folded lateral portion 62 has a first end portion 62A and a second end portion 62B (opposite ends in the longitudinal direction Y) distanced from each other in the longitudinal direction Y and an intermediate portion 62C extending between the first and second end portions 62A, 62B. The respective intermediate portions 61C, 62C of the first and second folded lateral portions 61, 62 extend on the outer sides in the transverse direction X of the absorbent body 33 in the absorbent region 21.

The topsheet 31 has a rectangular shape and covers the interior surface of the absorbent body 33 approximately over the entirety thereof. The topsheet 31 is formed of liquid-permeable fibrous nonwoven fabrics being capable of fastening and releasing the fastener 12 of the fastening system. As material for the topsheet 31, various types of fibrous nonwoven fabrics well known in the relevant technical field, for example, hydrophilized spunbond fibrous nonwoven fabrics, point-bond fibrous nonwoven fabrics or air-through nonwoven fabrics may be used. The mechanical fastening system is composed of the fastener 12 and a predetermined region of the topsheet 31, i.e., the nonwoven fabric defined so as to catch the fastener 12.

The backsheet 32 has a rectangular shape and lies on the exterior surface of the absorbent panel 11. The backsheet 32 is formed of hardly-liquid-permeable or liquid-impermeable fibrous nonwoven fabrics, moisture-permeable plastic films or laminate sheets thereof. When it is desired to use fibrous nonwoven fabrics as material for the backsheet 32, for example, spunbond/meltblown/spunbond (SMS) fibrous nonwoven fabrics or spunbond fibrous nonwoven fabrics may be used. The top- and backsheets 31, 32 have approximately the same dimensions in the longitudinal direction Y but a dimension in the transverse direction X of the topsheet 31 is smaller than a dimension in the transverse direction X of the backsheet 32 (i.e., a dimension W1 in the transverse direction X of the diaper 10).

The absorbent body 33 is formed of absorbent core materials and liquid-diffusible wrapping sheets (not shown) such as tissue paper to wrap the core materials. As the core materials, wood fluff pulp, superabsorbent polymer particles or fibers which are water-soluble and have water-absorption capacity at least 10 times as high as own mass thereof or a mixture of them, in any rate, molded in a desired shape may be used. While the absorbent body 33 is shaped in a rectangle extending in the longitudinal direction Y so far as the present embodiment is concerned, it is possible to shape the absorbent body 33 having a dimension in the transverse direction X gradually enlarged toward the middle in the longitudinal direction Y.

Figure 5:
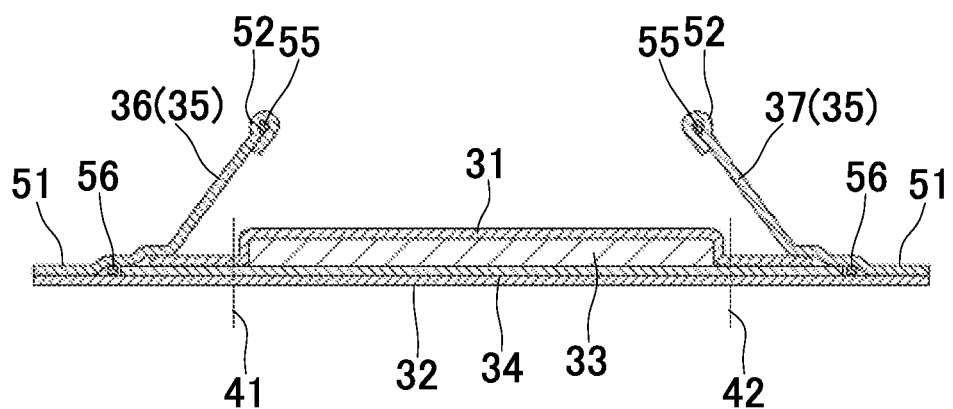
FIG. 5 is a schematic sectional view taken along line V-V in FIG. 3.

Referring to FIG. 5, the leakage-barrier sheet 34 is interleaved between the wrapping sheet of the absorbent body 33 and the backsheet 32 so as to cover the absorbent body 33 from the exterior surface thereof. As material for the leakage-barrier sheet 34, hardly-liquid-permeable, preferably liquid-impermeable but breathable plastic films may be used. A dimension in the longitudinal direction Y of the leakage-barrier sheet 34 is approximately the same as that of the backsheet 32 and a dimension in the transverse direction X of the leakage-barrier sheet 34 is larger than that of the topsheet 31 and smaller than that of the backsheet 32.

The containment sheet 35 includes a first containment sheet 36 lying on the side of the first side edge 15 and a second containment sheet 37 lying on the side of the second side edge 16. As material for the first and second containment sheets 36, 37, for example, hydrophobic SMS fibrous nonwoven fabrics or spunbond fibrous nonwoven fabrics may be used. The first and second containment sheets 36, 37 have proximal edge portions 51 respectively extending in the longitudinal direction Y and fixed to the both side edge portions of the absorbent panel 11, preferably to the both side edge portions of the backsheet 32 and sleeve-like or loop-like distal edge portions 52 lying on the inside of the respective proximal edge portions 51 as viewed in the transverse direction X. The first containment sheet 36 additionally includes a first end portion 53 and a second end portion 54 defined by end portions of the first containment sheet 36 in the longitudinal direction Y. At the proximal edge portions 51, the first end portion 53 and the second end portion 54, the containment sheets 35 are bonded to the respective sheets, for example, with hot melt adhesives.

Figure 6:
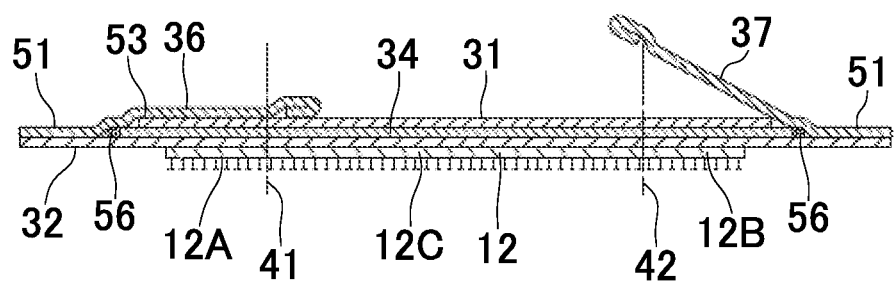
FIG. 6 is schematic sectional view taken along line VI-VI in FIG. 3.

Within each of the distal edge portions 52, at least one string- or strand-like containment-elastic element 55 extending in the longitudinal direction Y is contractibly secured under tension. With the article put on the body of pet animal, contraction of the containment-elastic element 55 causes the distal edge portion 52 to space away from the topsheet 31 toward the body of pet animal and to form a leakage-barrier against leakage of body exudates. The sectional views of FIGS. 5 and 6 illustrate the distal end portions 52 of the respective containment sheets 35 in an upstanding posture. According to the present embodiment, opposite ends in the longitudinal direction Y of the respective containment-elastic elements 55 are distanced from the first and second ends 13, 14. In each of the proximal edge portions 51, at least one lateral elastic element 56 formed of string- or strand-like elastic element and extending in the longitudinal direction Y is disposed between the containment sheet 35 and the backsheet 32 and contractibly secured under tension. The lateral elastic element 56 preferably extends from the first end edge 13 to the second end edge 14 so that the contractile force of the lateral elastic element 56 may act may perform action upon the whole area from the first end edge 13 to the second end edge 14. For joint of the respective sheets in the absorbent panel 11, the well known joint means, for example, hot melt adhesives may be used.

Referring to FIG. 6, the fastener 12 is located on the exterior surface of the backsheet 32 in the first non-absorbent region 22 so as to extend in the transverse direction X across the imaginary first and second longitudinal fold lines 41, 42 and has both end portions 12A, 12B located in the first and second folded lateral portions 61, 62 and an intermediate portion 12C located between the both end portions 12A, 12B. The fastener 12 overlaps the first and second containment sheets 36, 37 in a planar view. The fastener 12 includes a base material sheet bonded to the backsheet 32 and a plurality of hook elements rising from the base material sheet. These hook elements are adapted to be grabbed by and to be released from the top- and backsheets 31, 32. As material for the fastener 12, olefinic materials, for example, polyethylene, polypropylene or polyester resins may be used. The fastener 12 may be bonded to the backsheet 32, well known various types of bonding means such as hot melt adhesives though not shown. The hook elements may be replaced by pressure-sensitive adhesives though not also shown. When the pressure-sensitive adhesives are used, release layers are preferably located over a desired region so that the fastener may be releasably adhered.

A dimension L2 in the longitudinal direction Y of the absorbent body 33 is preferably in a range of about 20 to about 75% of a dimension in the longitudinal direction Y of the diaper 10 (i.e., a dimension in the longitudinal direction Y of the absorbent panel 11) L1 and more preferably about 50% or less of the dimension L1. The first non-absorbent region 22 and the second non-absorbent region 23 have an approximately the same dimension in the longitudinal direction Y. The dimension L2 of the absorbent body 33 may be set to 50% or less of the dimension L1 of the diaper 10 to restrict a tendency that the diaper 10 might become bulky due to the absorbent body 33, thereby doubling up the diaper 10 as compactly as possible.

A dimension L3 in the longitudinal direction Y of the fastener 12 is preferably larger than a dimension L4 in the longitudinal direction Y of a portion extending from the first end edge 13 to the end of the fastener 12 on the side of the first end edge 13 (hereinafter designated as a non-fastening portion). A dimension W3 in the transverse direction X of the fastener 12 is preferably larger than the dimension W2 in the transverse direction X of the absorbent body 33, preferably larger than a dimension W4 between the imaginary first and second longitudinal fold lines 41, 42 in the absorbent region 21 and preferably in a range of about 50 to about 90% of the dimension W1 in the transverse direction X of the diaper 10. A non-fastening region is provided between the fastener 12 and the first end edge 13 to assure that this non-fastening region may be pinched with one's fingers and the grabbing effect of the fastener may be easily released. Further, the dimension L3 of the fastener 12 is set to be larger than the dimension L4 of the non-fastening region to prevent the grabbing effect of the fastener 12 from being unintentionally released due to peeling off of the non-fastening region.

Figure 7:
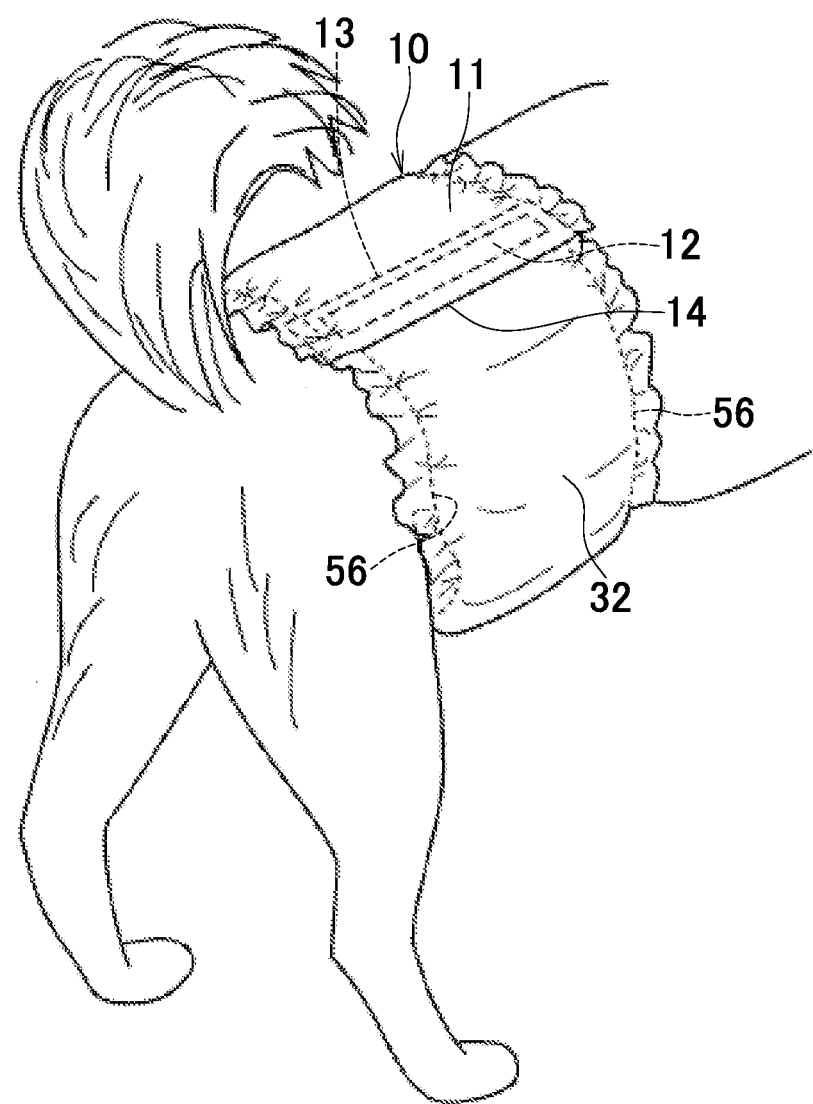
FIG. 7 is a diagram illustrating a state in which the diaper has been put on the body of pet animal.

Referring to FIG. 7, the diaper 10 is put on the body of pet animal so that the topsheet 31 faces the pet animal's body, the first containment sheet 36 lies on the head side of pet animal, the second containment sheet 37 lies on the buttock side of pet animal, the absorbent region 21 lies on the ventral side of pet animal, the first and second non-absorbent regions 22, 23 lie on the dorsal side of pet animal and finally the fastener 12 arranged on the exterior surface of the first non-absorbent region 22 is held on the interior surface (the topsheet 31) of the second non-absorbent region 23.

The dimension W3 in the transverse direction X of the fastener 12 set to be about 50% or more of the dimension W1 in the transverse direction X of the diaper 10 assures that the diaper 10 put on the body of pet animal is prevented from being displaced even when a waist dimension of pet animal significantly changes from the head toward the buttocks and the fit is sufficiently improved to prevent body exudates from leaking out. Further, the arrangement that the opposite ends in the longitudinal direction Y of the second containment sheet 37 are left free, brings about an advantageous effect as follows: When the first containment sheet 36 is positioned on the head side and the second containment sheet 37 is positioned on the buttock side to use the diaper 10 for a male pet animal, the both ends of the second containment sheet 37 which are left free, facilitates it to collapse the distal edge portion 52 of the second containment sheet 37 toward the buttock side and to position the penis between the first and second containment sheets 36, 37. Furthermore, the arrangement that the first containment sheet 36 has its both ends fixed at the first and second end portions 53, 54 is effective to restrict a possibility that the first containment sheet 36 might collapse toward the side of pet animal's head, thereby ensuring prevention of body exudates.

<Method of Folding the Diaper>

Figure 8:
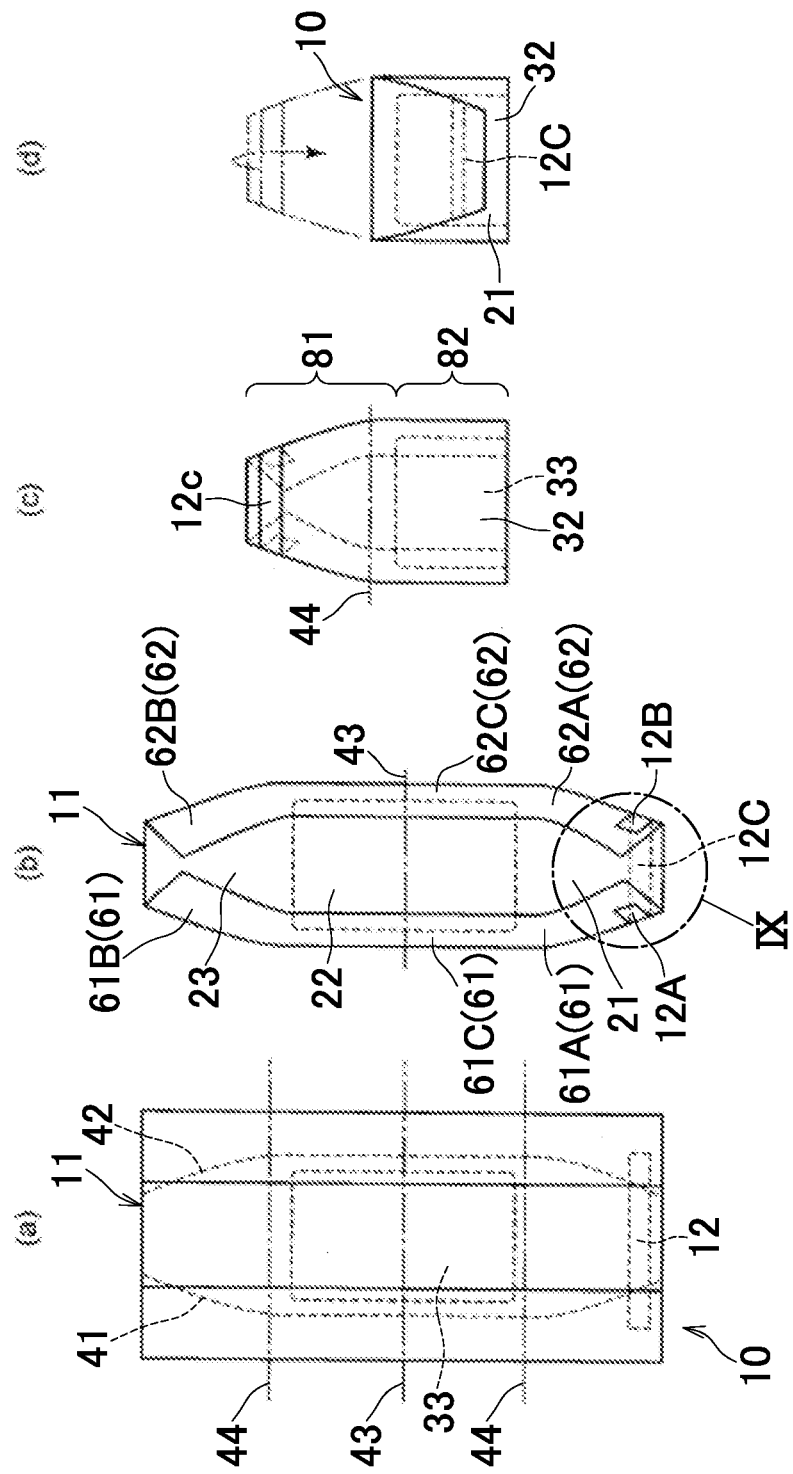
FIG. 8 (a) through FIG. 8 (d): diagrams exemplarily illustrating a method of folding the diaper.

Referring to FIG. 8 (a) through FIG. 8 (d), a method of folding the diaper 10 is exemplarily described. First, referring to FIG. 8 (a) and FIG. 8 (b), from a flatly developed state of the diaper 10, the first and second lateral portions 61, 62 are folded toward the side of the interior surface along the imaginary first and second longitudinal fold lines 41, 42, respectively. Then, referring to FIG. 8 (c), the diaper 10 is folded along the imaginary first transverse fold line 43 extending in the absorbent region 21 so that the exterior surface of the first non-absorbent region 22 and the interior surface of the second non-absorbent region 23 may face each other. In consequence of folding in this manner, the both end portions 12A, 12B of the fastener 12 are grabbed by the backsheet 32 at the respective second end portions 61B, 62B of the first and second folded portions 61, 62 facing the both end portions 12A, 12B of the fastener 12. While the imaginary first transverse fold line 43 overlaps the transverse axis Q so far as the present embodiment is concerned, the present invention includes another embodiment in which the imaginary first transverse fold line 43 lies closer to the first non-absorbent region 22 or closer to the second non-absorbent region 23 than to the transverse axis Q as long as the imaginary first transverse fold line 43 lies in the absorbent region 21. The present invention includes further embodiment in which the imaginary first and second longitudinal fold lines 41, 42 extend in parallel in the longitudinal direction Y in the first and second non-absorbent regions 22, 23.

Referring now to FIG. 8 (c) and FIG. 8 (d), a first lapped zone 81 of the diaper 10 in which the first and second non-absorbent regions 22, 23 is lapped over each other is further folded along the imaginary second transverse fold line 44 so that the first non-absorbent region 22 may lie on the interior side and the second non-absorbent region 23 may lie on the exterior side and the first lapped zone 81 is lapped over a second lapped zone 82 in which the absorbent body 33 is doubled up. In consequence of folding the diaper 10 in this manner, the first and second non-absorbent regions 22, 23 are lapped over the absorbent region 21 doubled up along the imaginary first transverse fold line 43 and the intermediate portion 12C of the fastener 12 is grabbed by the backsheet 32 of the absorbent region 21 facing the intermediate portion 12C. According to such second end edge 14 of folding, According to such method of folding, the first and second non-absorbent regions 22, 23 are fastened to each other under the effect of the fastener 12 at the both end portions 12A, 12B thereof and it is assured that any displacement of these non-absorbent regions during being folded along the imaginary second transverse fold line 44 is prevented. While it is essential that the imaginary second transverse fold line 44 overlaps at least any one of the first non-absorbent region 22 and the second non-absorbent region 23 in a planar view, the imaginary second transverse fold line 44 is preferably formed in the vicinity of the absorbent body 33 in the first lapped zone 81 in which the first non-absorbent region 22 and the second non-absorbent region 23 overlap each other.

Figure 4:
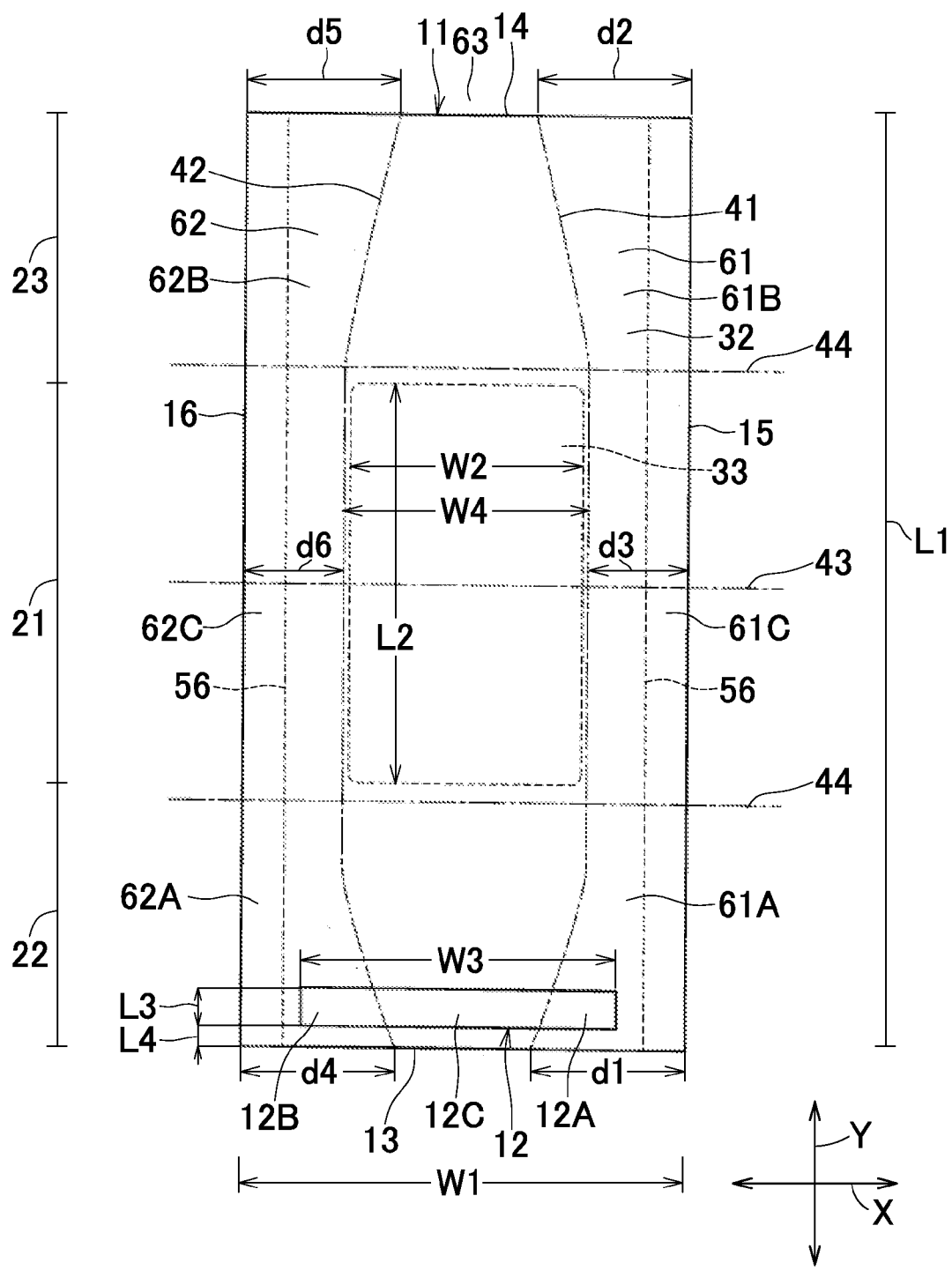
FIG. 4 is a developed perspective view of the diaper as viewed from the side of its exterior surface.

Referring to FIG. 4, according to the present embodiment, respective width dimensions (dimensions in the transverse direction X) d1, d2 of the first and second end portions 61A, 61B of the first folded lateral portion 61 are larger than a width dimension d3 of the intermediate portion 61C and width dimensions d4, d5 of the first and second end portions 62A, 62B of the second folded lateral portion 62 are larger than a width dimension d6 of the intermediate portion 62C. The term "width dimension" used herein means the maximum dimension in the transverse direction X in a planar view for the diaper 10 in a flatly developed state as illustrated in FIGS. 3 and 4. Specifically, the imaginary first and second longitudinal fold lines 41, 42 rectilinearly extend in the longitudinal direction Y on the outer sides in the transverse direction X of the absorbent body 33 and, in the first and second non-absorbent regions 22, 23, extend obliquely toward the longitudinal axis P. Preferably, the width dimensions d1, d2 of the first and second end portions 61A, 61B in the first folded lateral portion 61 are approximately the same and the width dimensions d4, d5 of the first and second end portions 62A, 62B are also approximately the same. In the first and second non-absorbent regions 22, 23, the imaginary first and second longitudinal fold lines 41, 42 may be rectilinear or curved. However, the first and second longitudinal fold lines 41, 42 are preferably provided in the curved form for the reason that the curved longitudinal fold lines 41, 42 restrict a possibility that folding propensity might be contracted, prevent the first and second non-absorbent regions 22, 23 from being folded along the imaginary first and second longitudinal fold lines 41, 42 when the diaper 10 is put on the body of pet animal and facilitate the both end portions 12A, 12B of the fastener 12 to be grabbed by the surface of the second non-absorbent region 23.

Figure 9:
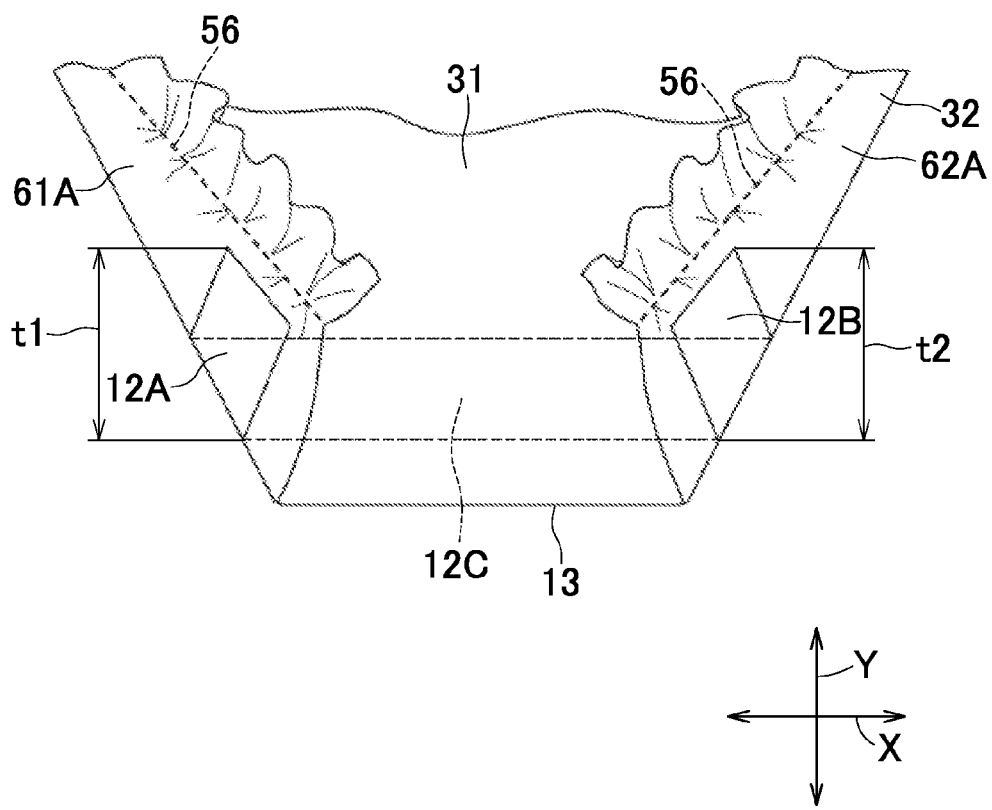
FIG. 9 is a scale-enlarged diagram illustrating a region IX in FIG. 8.

FIG. 9 is a scale-enlarged diagram of a region IX in FIG. 8. The fastener 12 extends in the transverse direction X beyond the imaginary first and second longitudinal fold lines 41, 42 so that the both end portions 12A, 12B of the fastener 12 may be folded back onto the intermediate portion 12C of the fastener 12. Dimensions t1, t2 in the longitudinal direction Y of the fastener 12 at the both end portions 12A, 12B are preferably larger than the dimension L3 in the longitudinal direction Y of the fastener 12. The terms "the dimensions t1, t2" in the longitudinal direction Y of the both end portions 12A, 12B mean distances in the longitudinal direction Y between end edges opposite in the longitudinal direction Y of the respective end portions 12A, 12B. As has been described above, the lateral elastic element 56 preferably extends to the first and second ends 13, 14 so that the first and second end portions 61A, 62A, 61A, 61B may be subjected to the contractile force of the lateral elastic element 56, thereby being easily maintained in the states folded along the imaginary first and second longitudinal fold lines 41, 42.

Figure 1:
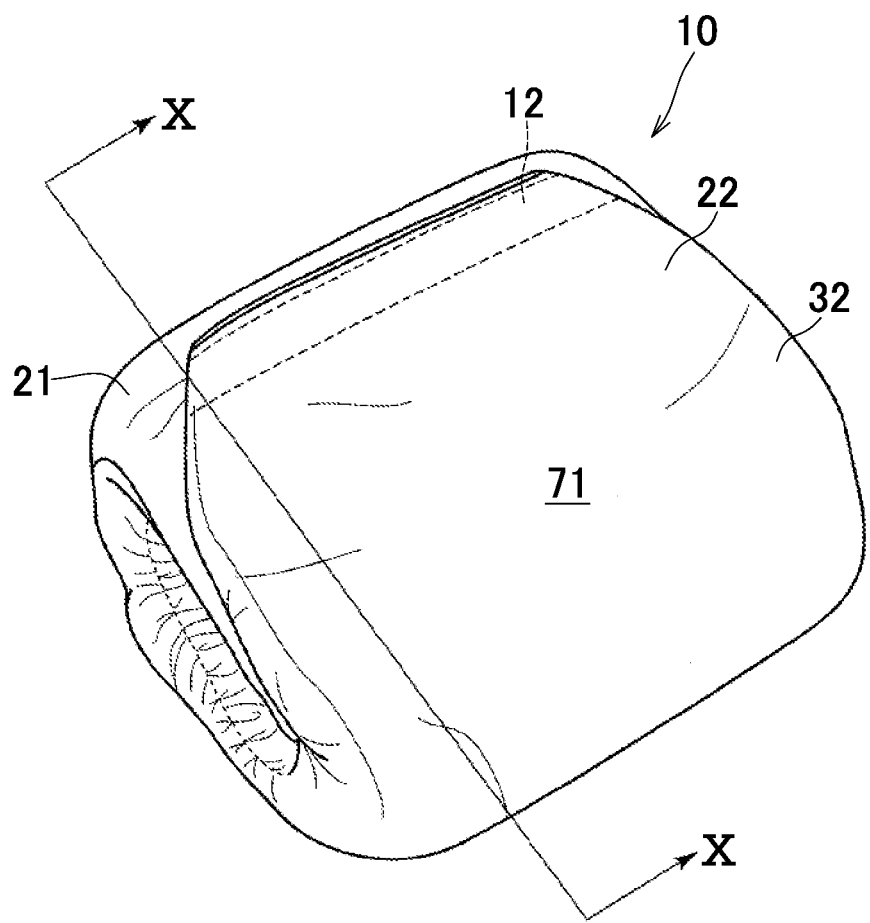
FIG. 1 is a perspective view exemplarily illustrating an absorbent article for pet animal in the form of a diaper in its doubled up state.
Figure 10:
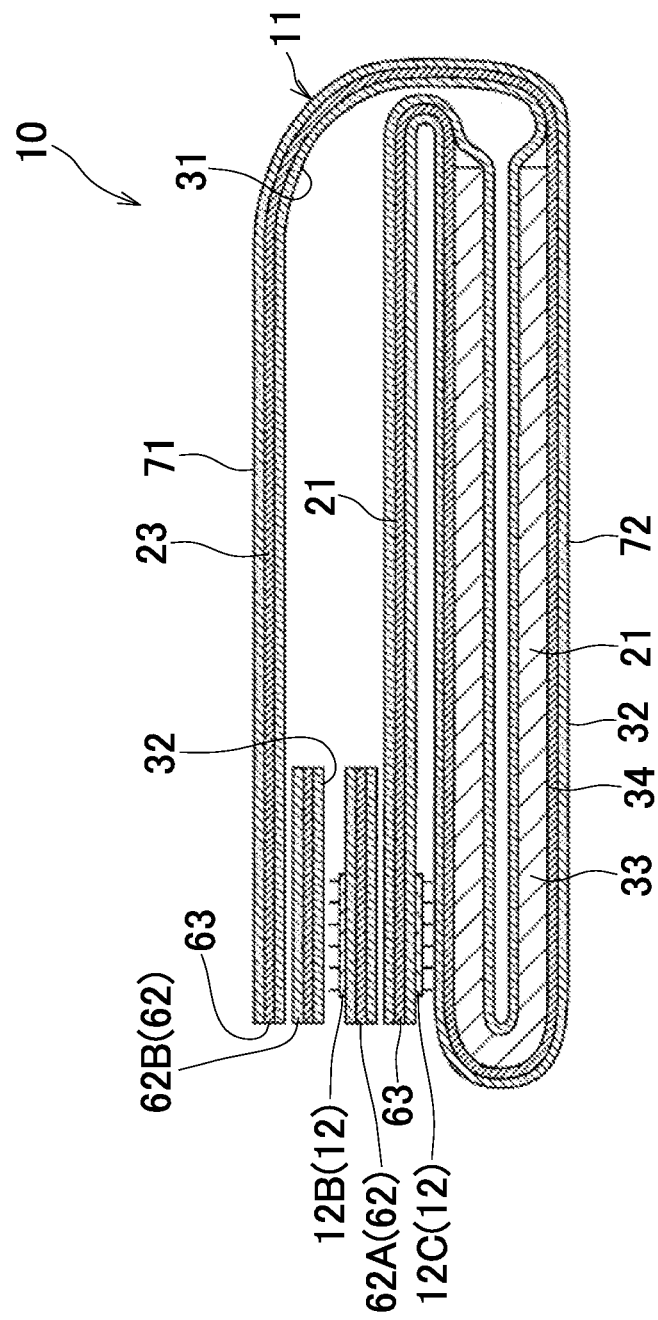
FIG. 10 is a schematic sectional view taken along a line X-X in FIG. 1.

Referring to FIG. 1 and FIG. 10, the diaper 10 in a folded state has a first exterior surface 71 and a second exterior surface 72 being opposite to the first exterior surface 71. The first exterior surface 71 is defined by the backsheet 32 in the second non-absorbent region 23 and the absorbent region 21 and the second exterior surface 72 is defined by the backsheet 32 in the absorbent region 21. The first non-absorbent region 22 and the second non-absorbent region 23 are fastened to each other by the intermediary of the both end portions 12A, 12B of the fastener 12 and the first non-absorbent region 22 and the absorbent region 21 are fastened to each other by the intermediary of the intermediate portion 12C of the fastener 12. The dimension W3 in the transverse direction X of the fastener 12 is larger than the dimension W4 between the first and second fold lines in the absorbent region 21 and the imaginary first and second longitudinal fold lines 41, 42 obliquely extend toward the longitudinal axis P in the first and second non-absorbent regions 22, 23. With such arrangement, a region over which the first non-absorbent region 22 and the second non-absorbent region 23 are engaged with each other by the intermediary of the both end portions 12A, 12B of the fastener 12 is relatively large. In consequence, it is possible to fasten the first and second non-absorbent regions at a correspondingly high fastening strength. In such diaper 10, the fastener 12 is grabbed by the backsheet 32 except the first non-absorbent region 22 and kept in a folded state and the fastener 12 is not exposed. For this reason, it is possible to avoid the anxiety that dust might adhere to the fastener 12 and deteriorate the fastening strength thereof.

Figure 11:
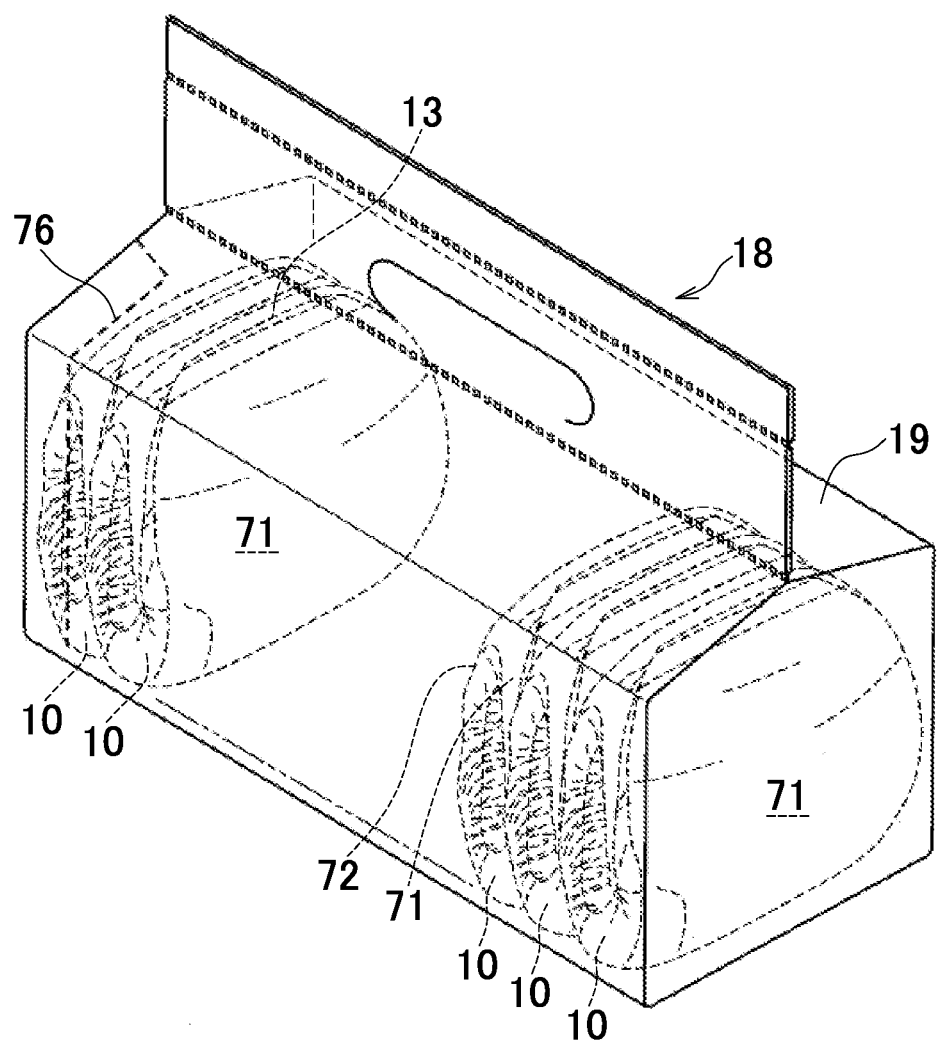
FIG. 11 is a perspective view exemplarily illustrating a package according to the present invention containing therein a plurality of the diapers.

FIG. 11 is a perspective view illustrating a package 18 containing a plurality of the diapers 10 each in a folded state. The package 18 includes a plurality of the diapers 10 and a packaging bag 19 to contain these diapers 10 therein. The packaging bag 19 has an openable portion 76 defined by perforations. A plurality of the diapers 10 are stacked in a manner that, in a pair of the adjacent diapers 10, the first exterior surface 71 of the one diaper 10 faces the second exterior surface 72 of the other diaper 10 and the first end edges 13 of the respective diapers 10 point to one and the same direction. In this regard, the state in which a plurality of the diapers 10 are stacked is not limited to the state as described above but it is also possible, for example, to stack the diapers 10 in a manner that, in a pair of the adjacent diapers 10, the first exterior surfaces 71 or the second exterior surfaces 72 thereof may face each other or in a manner that the respective first end edges 13 point to different directions.

If a plurality of the diapers are stacked with the respective fasteners exposed on the first or second exterior surfaces of the respective diapers as in the conventional package, already in a process of aligning the diapers, a handling person will face a bothersome problem such that the fastener of one diaper might be grabbed by the backsheet of the other diaper to interrupt an operation of aligning a plurality of the diapers and/or cause the articles to be wrinkled or torn. When it is desired to take out the diaper from the packaging bag one by one, the fastener on one diaper might be grabbed by the backsheet of the adjacent diaper and make it difficult to take out the diaper one by one. Even after the diaper has been taken out from the packaging bag, the fastener of this diaper might also grabbed by the other fibrous product. In contrast, in the diaper 10 and the package 18 thereof according to the present invention, the fastener 12 is not exposed and the individual diapers 10 are maintained in a folded state under the function of the fastener 12 so that the diapers 10 may be easily aligned and protected against being wrinkled and torn. Further, each pair of the adjacent diapers 10 is not engaged with each other by the intermediate of the fastener 12 and consequently it is easy to take out the diaper 10 from the packaging bag 19 one by one. In addition, it is possible to take out the diaper 10 maintained in a folded state from the packaging bag 19 one by one and, in consequence, the package according to the present invention has a high portability. The unexposed fastener 12 does not create a feeling of discomfort against the user when his or her fingers come in contact with the fastener during taking out the diaper 10 from the packaging bag 19 and that, after the diaper 10 has been taken out from the packaging bag 19, the fastener 12 might be grabbed by other fibrous products. Furthermore, the imaginary second transverse fold line 43 is allocated in the first lapped-over portion 81 in which the first and second non-absorbent region 22, 23 are lapped over each other and, consequentially, only the first lapped-over portion 81 in which the absorbent body 33 is not disposed is lapped over the second lapped-over portion 82. In this way, the absorbent body 33 is not lapped in three or more layers and thus it is possible to keep a thickness of the diaper 10 in its folded state relatively thin, thereby increasing the number of the diapers 10 contained in the packaging bag 19.

Figure 12:
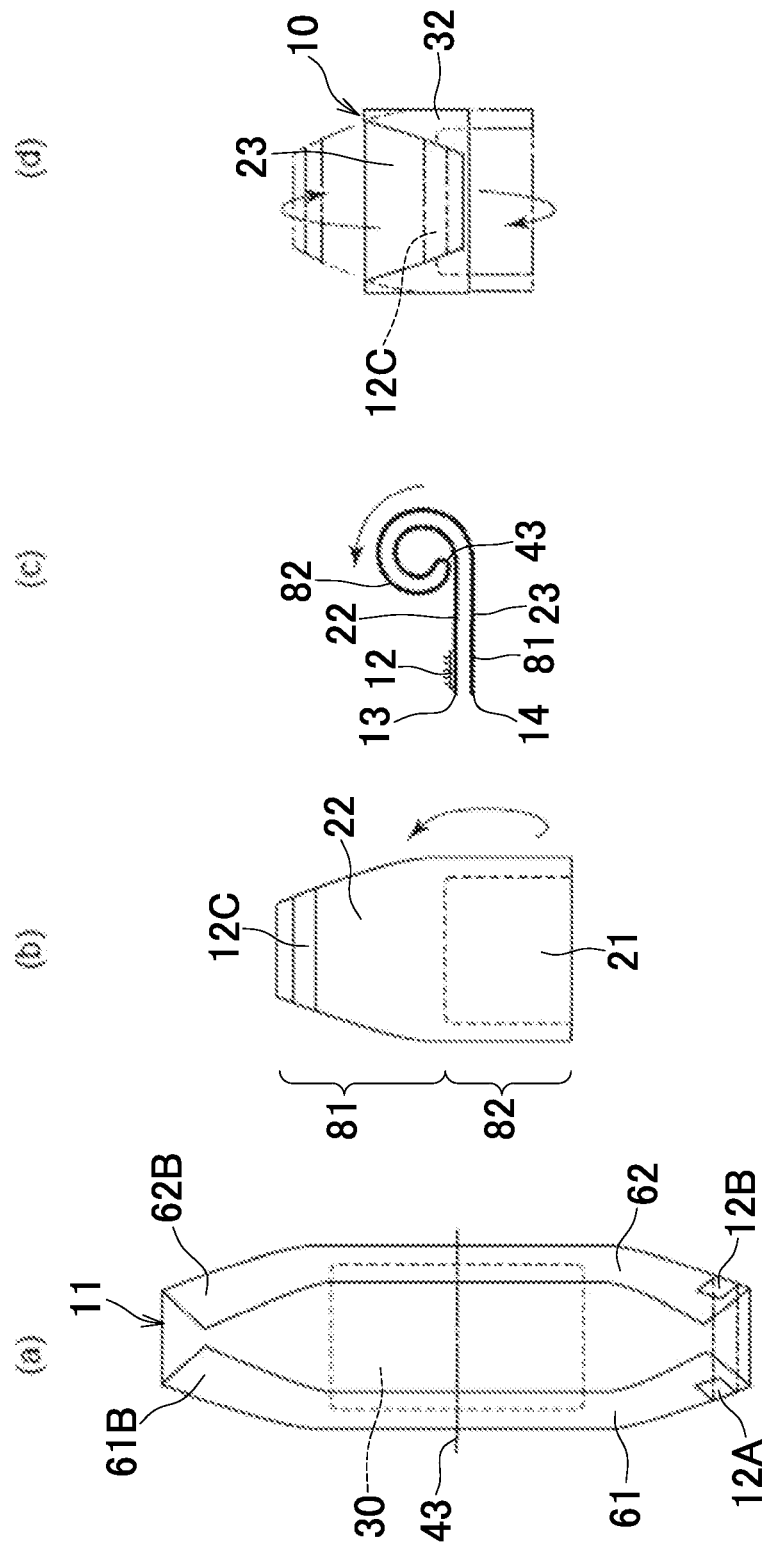
FIG. 12 (a) through FIG. 12 (d): diagram exemplarily illustrating another method of folding the diaper.

FIG. 12 is a diagram exemplarily illustrating another method of folding the diaper 10 wherein FIGS. 12 (*a*), (*b*) and (*d*) are plan views of the diaper 10 and FIG. 12 (*c*) is a schematic sectional view of the diaper 10. Referring to FIGS. 12 (*a*) and (*b*), the diaper 10 is folded along the imaginary first and second longitudinal fold lines 41, 42 and then folded along the imaginary first transverse fold line 43 allocated in the absorbent region 21. Referring now to FIGS. 12 (*c*) and (*d*), the second non-absorbent portion 82 over which the absorbent body 33 is lapped is folded as if rolled up toward the side of the first lapped-over portion 81 in which the fastener 12 is present (i.e., from the side of the imaginary first transverse fold line 43 to the side of the first and second end edges 13, 14). According to such method of folding, in the folded state, the both end portions 12A, 12B of the fastener 12 are respectively grabbed by the second end portions 61B, 62B of the first and second folded lateral portions 61, 62 and the intermediate portion 12C of the fastener 12 is grabbed by the backsheet 32 in the absorbent region 21 or the second non-absorbent region 23. According also to such method of folding, the fastener 12 is not exposed in the folded state of the diaper 10 to assure the effect as described above and, in addition thereto, it is possible to fold the diaper 10 more compactly. Furthermore, the diaper 10 is folded as if rolled up, and thus it is possible to restrict a possibility that folding propensities might be contracted.

FIG. 13 is a diagram exemplarily illustrating still another method of folding the diaper 10. Referring to FIGS. 13 (*a*) and (*b*), the diaper 10 is folded along the imaginary first and second longitudinal fold lines 41, 42 and then folded along the imaginary first transverse fold line 43 allocated in the absorbent region 21. Referring now to FIG. 13 (*b*) through (*d*), the first and second non-absorbent regions 22, 23 are folded along a plurality of the imaginary second transverse fold lines 44. Specifically, the imaginary second transverse fold lines 44 include a first line 45 and a second line 46 wherein, preferably, the first line 45 is arranged to be close to the fastener 12 but closer to the second lapped-over portion 82 than to the fastener 12 and the second line 46 is allocated between the first line 45 and the second lapped-over portion 82 but closer to the absorbent body 33. The diaper 10 is folded along the first line 45 so that the second non-absorbent region 23 may lie on the inner side and the first non-absorbent region 22 may lie on the outer side. Then the diaper 10 is folded along the second line 46 so that the second non-absorbent region 23 and the intermediate portion 12C of the fastener 12 may lie on the inner side. In this way, the intermediate portion 12C of the fastener 12 is grabbed by the backsheet 32 in the absorbent region 21.

The method of folding the diaper 10 described just above makes it possible to maintain the diaper 10 in a more firmly folded state than the diaper 10 folded according to two methods previously described. According to the methods of folding the diaper 10 as previously described, the backsheet 32 in the second non-absorbent region 23 defining part of the first exterior surface 71 is fastened by the both end portions 12A, 12B of the fastener 12 having engagement strength lower than that of the intermediate portion 12C of the fastener 12. In contrast, in the diaper 10 folded according to the present method of folding, the first non-absorbent region 22 defining part of the first exterior surface 73 is grabbed by the backsheet 32 in the absorbent region 21 by the intermediary of the intermediate portion 12C of the fastener 12 having a relatively high fastening strength. Consequently, the fastening effect should not be easily removed and the diaper 10 is reliably maintained in the folded state. Consequentially, the first and second non-absorbent regions 22, 23 should not peel off during carrying the individual diaper 10, thereby assuring a high portability.

The method of folding the diaper 10 is not limited to those exemplarily described in the present specification but, in order to ensure the advantageous inventive effects relating to the present embodiment, the fastener 12 extends in the transverse direction X beyond the imaginary first and second longitudinal fold lines 41, 42. While the first and second folded lateral portions 61, 62 are formed to be approximately the same in shape as well as in size according to the present embodiment, it is possible to arrange the first and second folded lateral portions 61, 62 so as to be different from each other in the width dimension. For example, it is possible to arrange the imaginary first longitudinal fold line 41 to extend in the longitudinal direction Y in parallel to the first folded lateral portion 61 so that the width dimension of the first folded lateral portion 61 may be constant and to arrange the imaginary second longitudinal fold line 42 extends obliquely in the first and second non-absorbent regions 22, 23 toward the longitudinal axis P so that the width dimension of the second folded lateral portion 62 may be enlarged in the first and second end portions 62A, 62B. One of the first and second folded lateral portions 61, 62, the width dimension at the first and/or second end portions is larger than the width dimension at the intermediate portion. It is essential for the diaper 10 according to the present invention that the fastener 12 is not exposed in the folded state of the diaper 10 and the folded state is maintained by the fastener 12. For example, it is possible to fold the diaper 10 along a plurality of fold lines extending in the transverse direction X in the absorbent region 21. Further, it is possible to arrange the diaper 10 so that the diaper 10 is not folded along the imaginary first and second longitudinal fold lines 41, 42, in other words, the diaper 10 has none of the first and second folded lateral portions 61, 62.

The disclosure relating to the present invention described hereinbefore may be arranged at least as follows.

The diaper 10 for pet animal having the longitudinal direction Y and the transverse direction X being orthogonal to each other and the internal surface and the external surface opposite to the internal surface, and including the absorbent panel 11 provided with the liquid-permeable topsheet 31 lying on the side of the interior surface and the liquid-impermeable backsheet 32 lying on the side of the exterior surface, and further including the fastening system functioning to fasten predetermined regions of the absorbent panel 11 to each other during use of the diaper 10 in a manner that a fastening effect may be released wherein: the absorbent panel 11 has the first end edge 13 and the second end edge 14 distanced from each other in the longitudinal direction Y and extending in the transverse direction X, the absorbent region 21 in which the absorbent body 33 is present, the first non-absorbent region 22 extending from the absorbent region 21 to the first end edge 13 and the second non-absorbent region 23 extending from the absorbent region 21 to the second end edge 14; and the fastening system includes a fastener 12 as the constituent thereof allocated on the exterior surface in the first non-absorbent region 22 and, in the state of the absorbent panel 11 folded at least in a manner that the interior surface of the first non-absorbent region 22 faces the interior surface of the second non-absorbent region 23, the fastener 12 is releasably grabbed by the exterior surface of the absorbent panel 11 except the first non-absorbent region 22 to maintain the folded state.

The package 18 containing a plurality of the diapers 10 wherein: the absorbent panel 11 is folded along the imaginary first transverse fold line 43 extending in the transverse direction X in the absorbent region 21 until the interior surface of the first non-absorbent region 22 and the interior surface of the second non-absorbent region 23 come in contact with each other and, in such folded state, further folded along the imaginary second transverse fold line 44 in the first lapped-over portion 81 in which the first non-absorbent region 22 and the second non-absorbent region 23 are lapped over each other; and the diaper 10 is maintained in the state folded along the imaginary first and second transverse fold lines 43, 44 by the intermediary of the fastener 12 and the fastener 12 is not grabbed by the other diapers 10 within the same package.

The aspects of the present invention having been disclosed in paragraphs and may include at least embodiments described below. These embodiments may be adopted separately or in combination.

(1) The absorbent panel 11 is folded along a plurality of imaginary transverse fold lines 43, 44 extending in the transverse direction X.

(2) The absorbent panel 11 has the pair of imaginary longitudinal fold lines 41, 42 distanced from each other in the transverse direction X and extending in the longitudinal direction Y and the pair of lateral portions 61, 62 folded toward the interior surface along the imaginary longitudinal fold lines 41, 42 wherein part of the fastener 12 extends outward in the transverse direction X beyond the imaginary longitudinal fold line 41 at least one 61 of the folded lateral portions.

(3) The dimension in the transverse direction X of at least one of the both end portions 61A, 61B in the longitudinal direction Y of the folded lateral portion 61 is larger than the dimension in the transverse direction X of an intermediate portion 61C defined between the both end portions 61A, 61B.

(4) The article is folded along the imaginary first transverse fold line 43 extending in the transverse direction X in the absorbent region 21 and the imaginary second transverse fold line 44 extending in the transverse direction X in the first non-absorbent region 22 and/or the second non-absorbent region 23.

(5) The dimension W3 in the transverse direction X of the fastener 12 is larger than a dimension W2 in the transverse direction of the absorbent body and the dimension L3 in the longitudinal direction Y of the fastener 12 is larger than the dimension L4 in the longitudinal direction Y of the portion extending between the fastener 12 and the first end portion 13.

(6) The dimension L2 in the longitudinal direction Y of the absorbent body 33 is 50% or less of the dimension L1 in the longitudinal direction Y of the absorbent panel 11.

{Reference Signs List}
10 diaper for pet animal (absorbent article for pet animal)
11 absorbent panel
12 fastener
18 package
19 packaging bag
21 absorbent region
22 first non-absorbent region
23 second non-absorbent region
31 topsheet
32 backsheet
33 absorbent body
41 imaginary first longitudinal fold line (longitudinal fold line)
42 imaginary second longitudinal fold line (longitudinal fold line
43 imaginary first transverse fold line (transverse fold line)
44 imaginary second transverse fold line (transverse fold line)
61 first folded lateral portion (folded lateral portion)
62 second folded lateral portion (folded lateral portion)
81 first lapped-over region
82 second lapped-over region

The invention claimed is:

1. An absorbent article for pet animal, said absorbent article comprising:
   a longitudinal direction and a transverse direction being orthogonal to each other,
   an internal surface and an external surface opposite to the internal surface,
   an absorbent panel provided with
      a liquid-permeable topsheet lying on the side of the internal surface,
      a liquid-impermeable backsheet lying on the side of the external surface, and
      a fastening system functioning to fasten predetermined regions of the absorbent panel to each other during use of the article in a manner that a fastening effect is released,
   wherein
   the absorbent panel further has
      a first end edge and a second end edge distanced from each other in the longitudinal direction and extending in the transverse direction,
      a first non-absorbent region extending from the absorbent region to the first end edge, and
      a second non-absorbent region extending from the absorbent region to the second end edge,
   the fastening system includes a fastener as a constituent thereof allocated on the external surface in the first non-absorbent region,
   in a state of the absorbent panel being folded at least in a manner that the internal surface of the first non-absorbent region faces the internal surface of the second non-absorbent region, the fastener is releasably grabbed by the external surface of the absorbent panel except the first non-absorbent region to maintain the folded state,
   the absorbent panel further has
      a pair of imaginary longitudinal fold lines distanced from each other in the transverse direction and extending in the longitudinal direction, and
      a pair of lateral portions folded toward the internal surface along the imaginary longitudinal fold lines, and
   a part of the fastener extends outward in the transverse direction beyond the imaginary longitudinal fold line in at least one of the folded lateral portions.

2. The absorbent article for pet animal according to claim 1, wherein the absorbent panel is folded along a plurality of imaginary transverse fold lines extending in the transverse direction.

3. The absorbent article for pet animal according to claim 1, wherein
   at least one of the first and second end edges in at least one of the pair of lateral portions has a dimension in the transverse direction larger than that of an intermediate portion of the at least one of the pair lateral portions, and
   said intermediate portion is defined between the first and second end edges in the longitudinal direction.

4. The absorbent article for pet animal according to claim 1, wherein the article is folded along
   an imaginary first transverse fold line extending in the transverse direction in the absorbent region, and
   an imaginary second transverse fold line extending in the transverse direction in the first non-absorbent region and/or the second non-absorbent region.

5. The absorbent article for pet animal according to claim 1, wherein
   the absorbent panel further includes an absorbent body,
   a dimension of the fastener in the transverse direction is larger than a dimension of the absorbent body in the transverse direction, and
   a dimension of the fastener in the longitudinal direction is larger than a dimension between the fastener and the first end edge of the absorbent panel in the longitudinal direction.

6. The absorbent article for pet animal according to claim 1, wherein
   the absorbent panel further includes an absorbent body, and
   a dimension of the absorbent body in the longitudinal direction is 50% or less of a dimension of the absorbent panel in the longitudinal direction.

7. A package, comprising:
   a plurality of absorbent articles for pet animal, each of the plurality of absorbent articles comprising:
   a longitudinal direction and a transverse direction being orthogonal to each other,
   an internal surface and an external surface opposite to the internal surface,
   an absorbent panel provided with
      a liquid-permeable topsheet lying on the side of the internal surface, and
      a liquid-impermeable backsheet lying on the side of the external surface, and
      a fastening system functioning to fasten predetermined regions of the absorbent panel to each other during use of the article in a manner that a fastening effect is released,
   wherein
   the absorbent panel further has
      a first end edge and a second end edge distanced from each other in the longitudinal direction and extending in the transverse direction,
      a first non-absorbent region extending from the absorbent region to the first end edge, and
      a second non-absorbent region extending from the absorbent region to the second end edge,
   the fastening system includes a fastener as a constituent thereof allocated on the external surface in the first non-absorbent region, and
   in a state of the absorbent panel being folded at least in a manner that the internal surface of the first non-absorbent region faces the internal surface of the second non-absorbent region, the fastener is releasably grabbed by the external surface of the absorbent panel except the first non-absorbent region to maintain the folded state, wherein
- the absorbent panel is folded along an imaginary first transverse fold line in the absorbent region until the first non-absorbent region and the internal surface of the second non-absorbent region come in contact with each other,
- in such folded state, the absorbent panel is further folded along an imaginary second transverse fold line in a lapped-over portion in which the first non-absorbent region and the second non-absorbent region are lapped over each other, and
- the absorbent article is maintained in the state folded along the imaginary first and second transverse fold lines by an intermediary of the fastener and the fastener is not grabbed by other absorbent articles within the package.

* * * * *